United States Patent
Corl et al.

(10) Patent No.: US 10,456,051 B2
(45) Date of Patent: Oct. 29, 2019

(54) PRESSURE SENSOR CALIBRATION SYSTEMS AND METHODS

(71) Applicant: Volcano Corporation, San Diego, CA (US)

(72) Inventors: Paul Douglas Corl, Palo Alto, CA (US); David H. Burkett, Temescula, CA (US); Douglas E. Meyer, Folsom, CA (US)

(73) Assignee: VOLCANO CORPORATION, San Diego, CA (US)

( * ) Notice: Subject to any disclaimer, the term of this patent is extended or adjusted under 35 U.S.C. 154(b) by 966 days.

(21) Appl. No.: 14/140,134

(22) Filed: Dec. 24, 2013

(65) Prior Publication Data
US 2014/0187985 A1 Jul. 3, 2014

Related U.S. Application Data

(60) Provisional application No. 61/747,458, filed on Dec. 31, 2012, provisional application No. 61/780,743, filed on Mar. 13, 2013.

(51) Int. Cl.
*A61B 5/0215* (2006.01)

(52) U.S. Cl.
CPC .. *A61B 5/02156* (2013.01); *A61B 2560/0252* (2013.01); *A61B 2562/226* (2013.01)

(58) Field of Classification Search
CPC ........ A61B 5/02; A61B 5/021; A61B 5/02156
USPC ......................................................... 600/486
See application file for complete search history.

(56) References Cited

U.S. PATENT DOCUMENTS

| | | | |
|---|---|---|---|
| 7,454,002 B1 * | 11/2008 | Gardner | A61B 5/0002 379/201.05 |
| 2004/0147969 A1 * | 7/2004 | Mann | A61B 5/0215 607/17 |
| 2006/0167351 A1 * | 7/2006 | Isaacson | A61B 5/1495 600/323 |
| 2007/0142727 A1 * | 6/2007 | Zhang | A61B 5/0031 600/486 |
| 2008/0312553 A1 * | 12/2008 | Timmons | A61B 5/02156 600/561 |
| 2009/0088650 A1 * | 4/2009 | Corl | A61B 5/0215 600/486 |

* cited by examiner

*Primary Examiner* — Puya Agahi

(57) ABSTRACT

Intravascular devices, systems, and methods are disclosed. In some embodiments, the intravascular devices include at least one pressure sensing component within a distal portion of the device. In that regard, one or more electrical, electronic, optical, and/or electro-optical pressure-sensing components is secured to an elongated member and the system includes components to process the output signals according to various calibration parameters.

8 Claims, 3 Drawing Sheets

PRESSURE SENSOR CALIBRATION SYSTEMS AND METHODS

CROSS-REFERENCE TO RELATED APPLICATIONS

The present application claims priority to and the benefit of U.S. Provisional Patent Application No. 61/780,743 filed Mar. 13, 2013 and U.S. Provisional Patent Application No. 61/747,458, filed Dec. 31, 2012, each of which is hereby incorporated by reference in its entirety.

BACKGROUND

The present disclosure relates generally to calibrating a pressure sensing device that can be used within the human body.

Pressure sensors suitable for insertion into the human body have been available for many years. These devices have been reduced in size such that they can now be placed in many different areas of the body including insertion into the vasculature. In one particular application, a miniature pressure sensor is mounted on a guidewire. The guidewire may be inserted into an artery and advanced into the coronary arteries supplying blood to the heart muscle. The guidewire can be positioned adjacent a stenosis to provide pressure information both proximal and distal to the lesion.

Due to their small size and manufacturing considerations, miniature pressure sensors have a significant degree of variability in their signal output. Such variability can include differing pressure sensitivities, zero pressure offsets, and temperature coefficients. To account for these variations, pressure sensors are typically calibrated as part of the manufacturing process and the calibration coefficients derived from that process are associated with the particular device.

In the intravascular pressure sensing system 10 shown in FIG. 1A, a guide wire 12 with a distal pressure sensor 14 is interconnected with the console via a series of connections and cables. The wire 12 is joined to the rotary connector cable 18 by a rotary connection assembly 16. On the proximal end of rotary cable 18 is a connection housing 20 that is joined to a patient interface module (PIM). The PIM is then connected to the console 50 via cable 24 through connection 26 joined to console connector 27. The connection housing 20 includes both the wires 30 leading to the pressure sensor 14 as well as a series of resistors 32. The resistors are selected during the calibration process at the manufacturing facility to encode the sensor calibration coefficients. When connected, the PIM 22 measures the resistor values to determine the calibration coefficients and then processes the raw sensor signals received on wires 30 accordingly. The PIM 22 then sends the calibrated signals through cable 24 on to the console for further processing.

In another form shown in FIG. 1B, the resistors disposed in the connector 20 have been replaced with an EEPROM 40. The cable is directly connected to the console 50. In this version the EEPROM is programmed with the calibration coefficients.

There remains a need for an improved system of calibrating pressure sensors and providing calibrated data signals to the processing console 50.

SUMMARY

The present disclosure provides calibration systems and methods for providing calibration information and/or calibrated sensor signals to a processing system.

In one form, the system includes a series of resistors holding calibration information and an associated microcontroller for reading the resistor values and translating the resistor-encoded calibration data to a digital format for delivery to the processing system.

In another form, the sensing system has stored calibration coefficients that are retained separate from the sensing guidewire. The stored calibration coefficients are provided to the processing console in advance of the sensing wire being activated and the processor then confirms that the sensing guidewire corresponds with an identifier associated with both the sensing guidewire and the calibration information. In one aspect, the console receives a plurality of stored calibration information in the form of a calibration database and then identifies the correct calibration information for a particular sensing guidewire from this calibration database based on a unique identifier associated with each sensing guidewire. In another aspect, a separate calibration memory device accompanies the sensing guidewire in the customer package. This separate calibration memory device can be read by the console either through a separate input port, such as a USB connection, or by first connecting the calibration memory device to console input where the sensing guidewire is normally connected, followed by removing the memory device and then connecting the sensing guidewire that same console input port.

In a still further form, the sensing system includes a signal pre-processing system incorporated between the sensing guidewire and the console. The pre-processing system receives the raw signals from the sensor positioned in the body, applies various processing techniques to the raw signals based on calibration information stored in memory, and outputs calibrated signals to the system console that require no further processing to provide accurate measurements. In a preferred form, the pre-processing system has a small form factor and substantially fits within the strain relief portion of the cable to console connector assembly.

These and other aspects of the present disclosure will be described and become apparent from the following description.

BRIEF DESCRIPTION OF THE DRAWINGS

The present disclosure is best understood from the following detailed description when read with the embodiments, or examples, illustrated in the accompanying figures. It is emphasized that various features are not necessarily drawn to scale. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

DETAILED DESCRIPTION

Figure 1A:
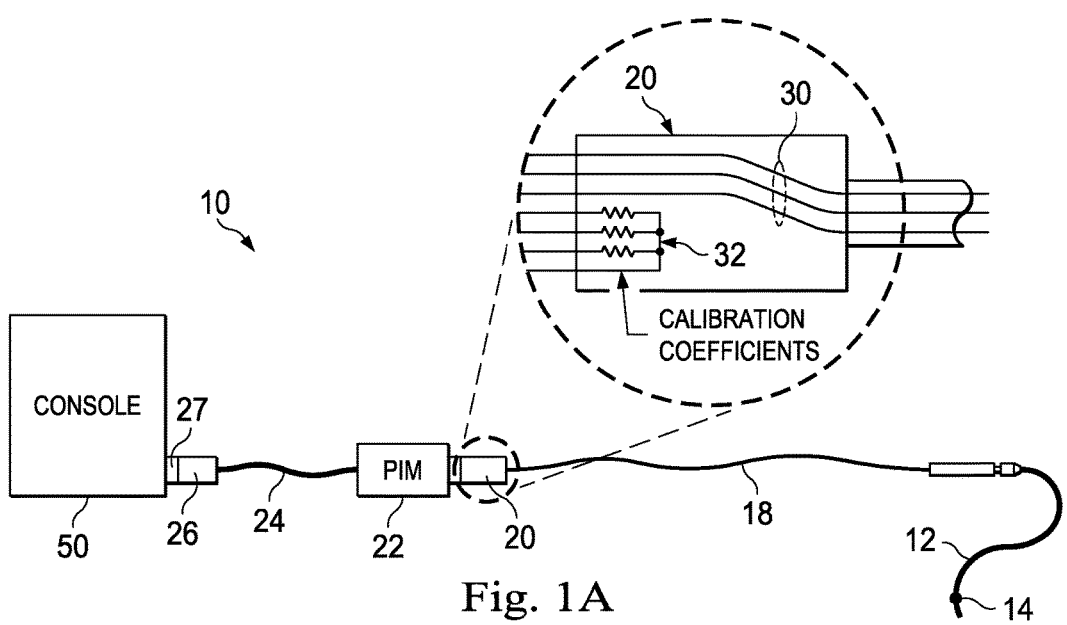
FIGS. 1A and 1B are examples of existing systems having pressure sensing guidewires connected to processing consoles.
Figure 1B:
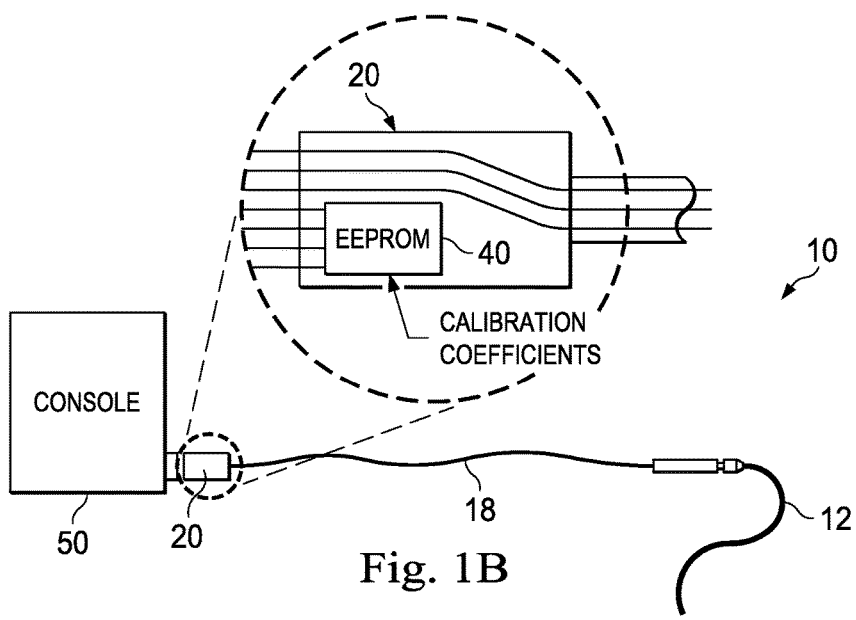

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one of ordinary skill in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In some embodiments, the flexible elongate member of sensing guidewire or catheter of the present disclosure includes one or more electronic, electrical, mechanical, electromechanical, electromagnetic, piezoelectric, optical, or electro-optical sensing components. For example, without limitation, a flexible elongate member may include one or more of the following components: a pressure sensor, a temperature sensor, a flow sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display, and as such, they may require calibration or other characterization information to be associated with the particular sensor or device. In some aspects, embodiments of the present disclosure include imaging devices for imaging within the lumen of a vessel, including both medical and non-medical applications. However, some embodiments of the present disclosure are particularly suited for use in the context of human vasculature.

The sensing components of the present disclosure are often disposed within a distal portion of the flexible elongate member. As used herein, "distal portion" of the flexible elongate member includes any portion of the flexible elongate member from the mid-point to the distal tip.

The sensing components and the associated communication lines are sized and shaped to allow for the diameter of the sensing guidewire or catheter to be very small. For example, the outside diameter of the flexible elongate member, such as the guidewire, containing one or more sensing components as described herein are from about 0.007" (0.18 mm) to about 0.118" (3.0 mm), with some particular embodiments having outer diameters of approximately 0.014" (0.36 mm), approximately 0.018" (0.46 mm), and approximately 0.035" (0.89 mm). As such, the flexible elongate members incorporating the sensing component(s) of the present application are suitable for use in a wide variety of lumens within a human patient besides those that are part of or immediately surround the heart, including veins and arteries of the extremities, renal arteries, blood vessels in and around the brain, and other lumens.

Figure 2:
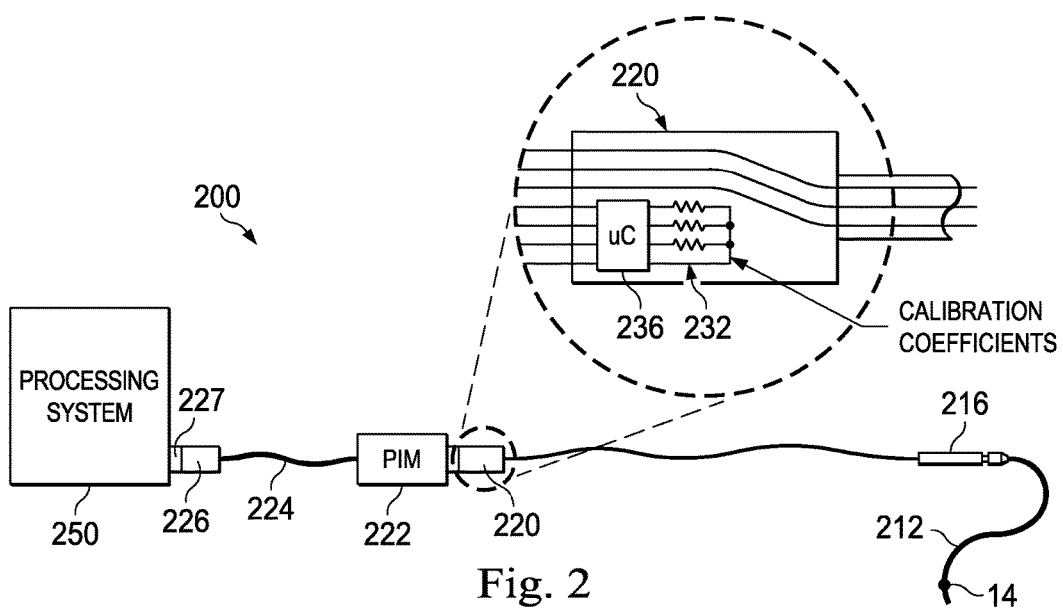
FIG. 2 illustrates an embodiment of a sensing guidewire connection system.

Referring now to FIG. 2, there is shown an embodiment of one aspect of the present disclosure. In the system of FIG. 2, the system 200 includes the sensing member 14 mounted on a flexible member 212 which is interconnected with coupler 216. Coupler 216 has a connector assembly 220 that attaches to the patient interface module (PIM) 222. Similar to the embodiment of FIG. 1A, the PIM is connected to the processing console 250 via cable 224 and a connection between coupler 226 and 227. As shown in the enlarged view of connector 220, a series of resistors 232 are positioned within connection assembly 220 to encode sensor calibration coefficients. A microcontroller 236 is provided to measure the resistor values and translate those values into a set of calibration coefficients for the sensor. The resistors 232 are soldered onto a small printed circuit board (PCB) along with the interconnected microcontroller 236. In effect, the set of resistors represents an analog read-only memory for calibration coefficients, and the microcontroller serves as an interface to translate those analog resistance values into a convenient digital format. In one aspect, the microcontroller 236 includes an analog to digital converter, a multiplexer, and an I2C interface. These capabilities can be found in a mixed signal processor such as commercially available MSP430 microcontroller sold by Texas Instruments. In the illustrated embodiment, the microcontroller can be programmed to emulate the EEPROM found on existing systems such that the devices are backwardly compatible with existing PIM systems. In this embodiment, when the PIM attempts to read the address range previously allocated for the EEPROM, the microcontroller responds with the calibration coefficients determined by translating the measured resistor values into the appropriate digital format. The calibration information is stored in a set of resistors, selected at the time of calibration, but then read by the ADC and translated into a convenient digital format by the microcontroller at the time of use. This system utilizes the prior technique of using resistor values to encode wire calibration and characteristic information, while incorporating a microcontroller to translate the resistor-encoded information into a convenient digital format, all within the confined form factor of the connector housing of the guidewire coupling cable.

In a further aspect, in addition to providing calibration information, the microcontroller can have a memory. The memory can be used to store the serial number and model number for the associated guidewire such that the system will properly recognize the wire and record the appropriate serial number. In a further aspect, the memory may also include calibration values or expected resistor values. In this manner, the microcontroller can measure the actual resistor values and compare them to the expected resistor values. Alternatively, calibration values can be stored in memory and the system can compare calibration values derived from the resistor measurements to the memory-based calibration values. Although the stored calibration information in memory would not be passed on to the processing system, in the case of a significant disagreement between these values, the system would report an error, and the wire would be rejected for use. This would prevent erroneous calibration coefficients, caused by resistor measurement error or other malfunction, from being used with a particular sensing component.

Figure 3A:
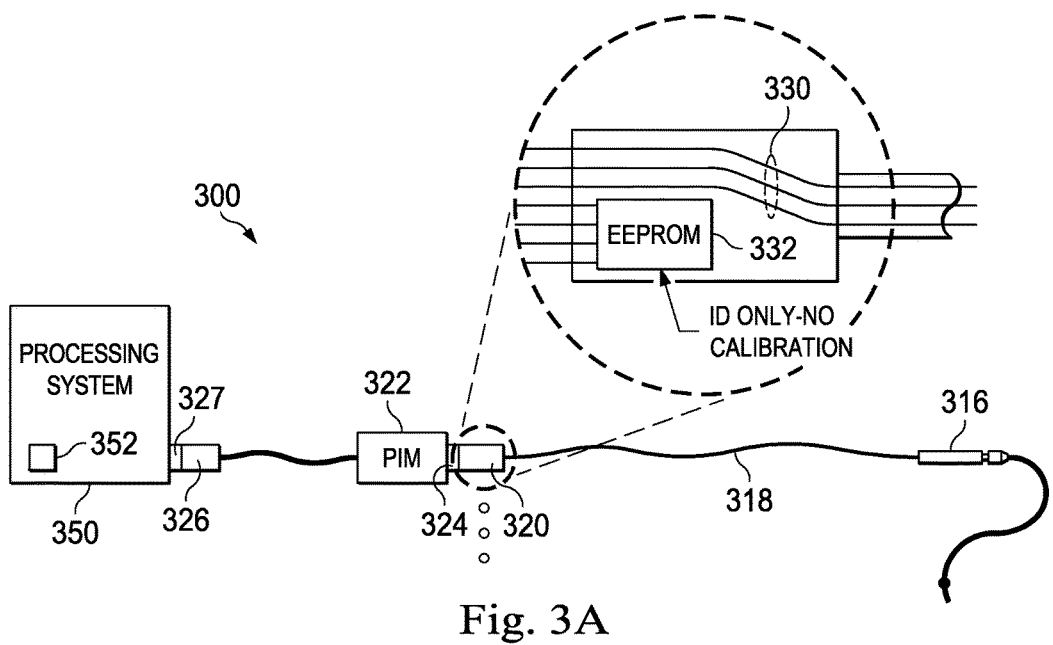
FIGS. 3A and 3B illustrate a further embodiment of a sensing guidewire connection system.
Figure 3B:
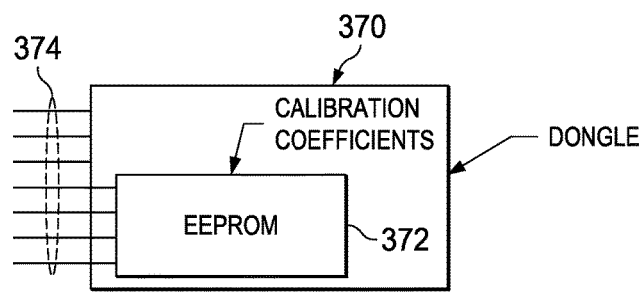

Referring now to FIG. 3A, there is shown a further embodiment of a pressure sensing system 300. In the system of FIG. 3, the system 300 includes a coupler 316 configured to receive a sensing guidewire or catheter. The coupler 316 has a cable 318 and a connector assembly 320 that attaches to the patient interface module (PIM) 322 via connector 324. Similar to the embodiment of FIG. 1A, the PIM is connected to the processing console 350 via a connection between coupler 326 and 327. In the illustrated embodiment, an EEPROM 332 is provided in the rotary cable connector assembly 320 along with the sensor data communication lines 330. However, the EEPROM 332 includes only serial number or other unique identifier information without the corresponding calibration coefficients. The calibration coefficients are separately provided to the system. In one embodiment, on a periodic basis, the system console 350 is updated with all of the calibration data for the available previously manufactured sensing devices. In another embodiment, the system console has network access and looks up the calibration information from a central database for each serial number as each wire is registered with the system.

With the described system, a unique serial number can be applied to each device early in the manufacturing process and the calibration data can be determined later and then forwarded separately for use by processing systems already deployed in the field.

In a related aspect, the calibration information developed later in the manufacturing process may be stored on a separate memory device that is then packaged with the sensing device. More specifically, referring now to FIG. 3B, there is shown still a further feature of a pressure sensing system. In the illustrated embodiment, the system includes a dongle 370 having a memory 372 and an external connection 374. If the external connection is a USB type, the dongle may be received within a USB port 352 within the console or a similar port in the PIM. The dongle would contain the calibration coefficients for one or more pressure sensing guidewires. In use, the dongle would be plugged into the Pimette or the system, which would then download the calibration coefficients from the dongle. The wire would be connected to the Pimette as well and the output of the sensors on the guidewire would be calibrated according to the coefficients stored on the dongle. In one aspect as illustrated in FIG. 3A, the rotary cable retains at least some memory element sufficient to hold a serial number. The dongle would also be provided with this information such that the system and/or Pimette can verify that the serial number of the pressure sensing guidewire corresponds to the calibration coefficients received from the Dongle.

In another aspect, a single dongle may contain the calibration coefficients for many guidewires. For example, a single dongle may be shipped with a large shipment of guidewires to a single hospital. Alternatively, for large hospital facilities with more than one catheter lab, a dongle for each catheter lab can be shipped, with each dongle containing the calibration information for all of the wires in the shipment. In this way, the dongle could be maintained in the Pimette or console through the course of many months until a new shipment of wires is received by the catheter lab facility. In this arrangement, the system console and/or the Pimette may check to see if a guidewire connected to the system has a serial number of a wire that has already been used by the system. In this way, patients can be protected from inadvertent or intentional reuse of the one-time use only pressure sensors. Still further, the dongle may include a memory component tracking which of the guidewires from its memory have been used.

In still a further aspect, the PIM includes an input port 324 which in the illustrated version is a 10-pin RJ-50 connector rather than a standard computer interface such as a USB port. The 10-pin RJ-50 connector is configured to receive a cable connection from the sensor wire interface. In the illustrated embodiment of FIG. 3A, the sensing wire system also includes the standard 10-pin RJ-50 connector cable for coupling the sensing wire to the processing system along with a separate dongle shown in FIG. 3B having the same 10-pin RJ-50 connector configured to be received by the PIM. The processing system includes a program that is designed to read the sensing wire serial number, calibration and other information on the dongle when attached to the 10-pin RJ-50 connector. In addition, the processing system includes a separate programmed sequence that recognizes the dongle as a data transfer device rather than an actual sensing wire and begins a dongle data transfer subroutine. A portion of the subroutine communicates with the primary sensor program that the dongle is not a sensing wire and the primary program may be suspended until an actual sensing wire is connected to the system. Once the dongle information is downloaded to the system, in a next step, the system prompts the user to remove the dongle and insert the 10-pin RJ-50 connector of the rotary cable. The system then checks the serial number of the sensing guidewire stored on the wire or connection cable with the serial number obtained from the dongle. If the numbers are consistent, then the system advises the user that there has been a match and the user can proceed with using the sensing guidewire within a patient, while proceeding to utilize the dongle calibration information for processing the sensed signals from the sensing guidewire.

In use, the user would insert the dongle into the processing system as an initial step. The processing system would then read the information from the dongle and verify that it corresponds to processing features of the processing system including that the sensor associated with the dongle is of a type that is supported by software currently loaded on the processing system. In addition, if the processing system is a multi-modality system, the system would read the sensor type from the dongle and initiate software processing modules and user interfaces associated with the sensor type identified by the dongle. In addition, the sensor wire serial number, lot number, identifying characteristics, calibration coefficients, and other information is read from the dongle by the processing system. The dongle also contains a data set that is read by the processing system to indicate that it is a data transfer device, not an actual sensing guidewire. Once the dongle information has been transferred from the dongle to the processing system and the processing system verifies that the dongle is associated with a supported sensing device, the system then prompts the user via a user interface, such as a display screen, to remove the dongle and insert the connector of a sensing wire to the processing system. Once the sensing wire is connected to the processing system, the sensing and processing of data can continue according to existing practices.

Figure 4:
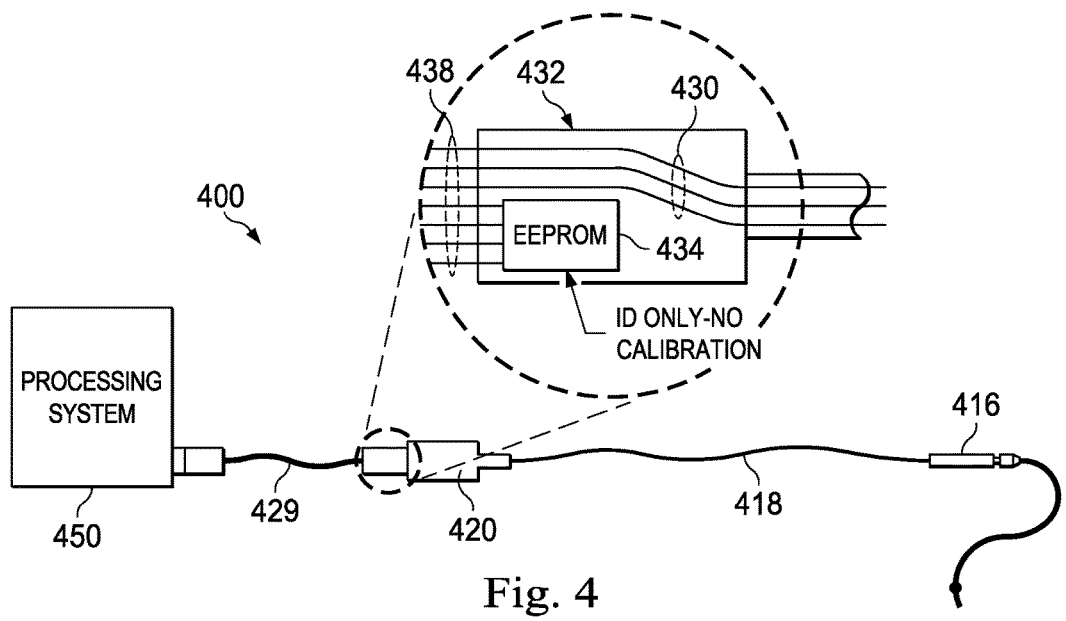
FIG. 4 illustrates still a further embodiment of a sensing guide wire connection and processing system according to a further aspect of the present disclosure.

Referring now to FIG. 4, there is shown still a further guidewire sensing system 400 according to a further aspect of the present disclosure. As shown, the PIM from the previous embodiments is no longer present. The sensing wire connector 416 is joined by cable 418 and connector 420 directly to the processing console 450. In this embodiment, a signal processor 432 can act on the raw sensor signals received from conductors 430 according to calibration coefficients stored in memory 434. These processed and compensated signals can then be passed through connection pins 438 extending into connection assembly 427 of the cable 429 connected directly to the console 450 for further processing. In an alternative form, the processing circuitry 432 could be configured through firmware to not perform the compensation of the pressure sensor, and instead only pass along raw uncompensated data to the console 450 for compensation within the system. The circuitry 432 can be based on a high resolution (24-bit) ADC, so that it can accommodate the full range of uncompensated sensor outputs with the needed resolution. This scheme could potentially use the rotary cable and calibration EEPROM system mentioned above to provide the processing console 450 with this information if the processing circuitry 432 will not perform the compensation operations. Additional features concerning the operation of such components can be found in application Ser. No. 61/747,140 entitled INTRAVSCULAR DEVICES HAVING INFORMATION STORED THEREON AND/OR WIRELESS COMMUNICATION FUNCTIONALITY, INCLUDING ASSOCIATED DEVICES, SYSTEMS AND METHODS, filed Dec. 28, 2012 the contents of which are hereby incorporated by reference in their entirety.

One subtlety of this scheme is related to how the temperature compensation is implemented. Note that the offset/zero/normalization and scale factor compensation are easily performed within the processing system 450. For temperature compensation, the system of FIG. 4 could use equal current excitation of both legs of the sensor, combined with mathematical computation in the system to implement temperature compensation. Alternatively, it could rely on unbalanced currents supplied by the system to implement the first order temperature compensation. Finally, the circuitry 432 could include programmable current sources, programmed from the system, to implement the first order temperature compensation.

Persons of ordinary skill in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular sensor assembly, comprising:
   a flexible elongate member comprising:
      a proximal connection portion configured to be positioned outside a patient body and adapted for coupling to a signal processing system via a patient interface module (PIM) communicatively positioned between the flexible elongate member and the signal processing system, and
      an intravascular sensor disposed adjacent a distal end of the flexible elongate member and configured to be positioned within the patient body,
      wherein the proximal connection portion comprises a cable and a connector at a proximal portion of the cable, the connector comprising a connector housing;
   a memory component disposed within the connector housing of the connector and storing one or more calibration coefficients for the intravascular sensor; and
   a processor disposed within the connector housing of the connector, the processor configured to:
      receive sensor signals from the intravascular sensor;
      read the one or more calibration coefficients from the memory component in response to communication by the PIM;
      calibrate the sensor signals based on the one or more calibration coefficients such that the sensor signals are calibrated within the flexible elongate member during use of the intravascular sensor assembly; and
      output calibrated sensor signals from the connector to the PIM.

2. The assembly of claim 1, wherein the memory component comprises an analog read only memory.

3. The assembly of claim 2, wherein the memory component comprises resistors.

4. The assembly of claim 2, wherein the processor comprises an analog to digital converter and a multiplexer.

5. The assembly of claim 4, wherein the processor further comprises an I2C interface.

6. The assembly of claim 1, wherein the PIM comprises a second cable disposed between the connector housing and the signal processing system.

7. The assembly of claim 1, wherein the connector housing is configured to connect to a second connector of the PIM.

8. An intravascular sensing system, comprising:
   a flexible elongate member comprising:
      a proximal connection portion configured to be positioned outside a patient body, the proximal connection portion comprising a cable and a connector at a proximal portion of the cable, wherein a memory component storing one or more calibration coefficients for the intravascular sensing system and a processor are disposed within a connector housing of the connector; and
   as intravascular sensor disposed adjacent a distal end of the flexible elongate member and configured to be positioned within the patient body; and
   a patient interface module (PIM) separate from the flexible elongate member, the PIM adapted for coupling the proximal connection portion to a signal processing system, wherein the processor is configured to:
      receive sensor signals from the intravascular sensor;
      read the one or more calibration coefficients from the memory component in response to communication by the PIM;
      calibrate the sensor signals based on the one or more calibration coefficients such that the sensor signals are calibrated within the flexible elongate member during use of the intravascular sensing system; and
   output calibrated sensor signals from the connector to the PIM, and wherein the PIM is configured to receive the calibrated sensor signals output by the connector.

\* \* \* \* \*